United States Patent [19]

Töpfl et al.

[11] Patent Number: 4,992,434
[45] Date of Patent: Feb. 12, 1991

[54] MICROBICIDAL COMPOSITION

[75] Inventors: Werner Töpfl, Dornach; Robert Nyfeler, Basel; Werner Föry, Riehen, all of Switzerland

[73] Assignee: Ciba-Geigy Corporation, Ardsley, N.Y.

[21] Appl. No.: 336,166

[22] Filed: Apr. 11, 1989

Related U.S. Application Data

[63] Continuation-in-part of Ser. No. 147,388, Jan. 25, 1988, abandoned.

[30] Foreign Application Priority Data

Jan. 30, 1987 [CH] Switzerland .......................... 351/87

[51] Int. Cl.$^5$ .................... C07D 277/56; A01N 43/78
[52] U.S. Cl. .................... 514/212; 514/227.8; 514/236.8; 514/326; 514/365; 540/524; 540/603; 544/60; 544/133; 546/209; 548/147; 548/200; 548/201
[58] Field of Search ............... 548/200, 147; 514/365, 514/212, 227.8, 236.8, 326; 540/524, 603; 544/60, 133; 546/209

[56] References Cited

U.S. PATENT DOCUMENTS 4,602,937 7/1986 Howe et al. ........................ 71/90

FOREIGN PATENT DOCUMENTS 0064353 11/1982 European Pat. Off. ............... 71/90
2020662 11/1979 United Kingdom ................. 7/90

OTHER PUBLICATIONS

Craig et al., Phytopathology, 77, 1530 (1987).

*Primary Examiner*—Robert Gerstl
*Attorney, Agent, or Firm*—George R. Dohmann

[57] ABSTRACT

A microbicidal compostion contains as active ingredient 2-chloro-4-trifluoromethylthiazol-5-carbonic acid derivatives of the formula I

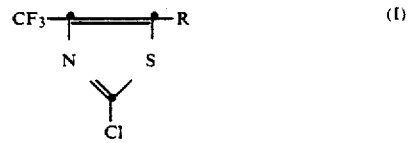

R is organic radical with up to 40 carbon atoms, which optionally contains nitrogen, oxygen or sulfur atoms and which can be transformed by hydrolosis or oxydation into the directly to the thiazol ring bound carboxyl rest. These compounds have good microbicidal activity and are used for the control and prevention of infestation of plants by phytophathogenic microorganisms.

11 Claims, No Drawings

MICROBICIDAL COMPOSITION

This is a continuation-in-part of our application Ser. No. 147,388, filed Jan. 25, 1988, now abandoned.

The present invention relates to a microbicidal compositions which contain as active ingredient a 2-chloro-4-trifluoromethyl-thiazol-5-carbonic acid derivative of formula I, to the preparation of these derivatives and to compositions containing them, as well as to methods for controlling or preventing infestation of plants by phytopathogenous microorganisms.

The 2-chloro-4-trifluoromethyl-thiazol-5-carbonic acid derivatives correspond to the formula I

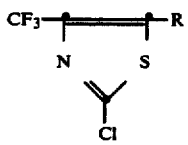

wherein R is an organic radical with up to 40 carbon atoms which optionally contains nitrogen, oxygen or sulfur atoms and which can be transformed by hydrolysis or oxidation into the directly to the thiazol ring bound carboxyl rest.

Thiazol-5-carbonic acid derivatives are known from the literature. 2,4-Dimethylthiazol-5-carboxamides are disclosed as fungicides in U.S. Pat. No. 3,725,427; 2-chloro-4-trifluoromethylthiazol-5-carbonic acid derivatives are disclosed as antidotes (safeners) to reduce the phytotoxic action of strong herbicides on cultivated plants in U.S. Pat. Nos. 4,199,506, 4,251,261, 4,308,391, 4,437,875, 4,437,876 and 4,640,702 and in the published European patent applications No. 27,018, 44,201 and 63,353.

It has been found that the 2-chloro-4-trifluoromethyl-thiazol-5-carbonic acid derivatives of formula I have extraordinary good microbicidal activity and are able to protect cultivated plants from infestation by phytopathological microbes and fungi or cure them of such infestation.

The compounds of formula I are stable at room temperature. They can be used in the agricultural sector or related fields for controlling pests especially preventively and curatively for the control of phytopathogenic microorganisms. The derivatives of formula I are characterized by excellent fungicidal activity over a wide concentration range and by unproblematic handling. These derivatives further possess nematicidal properties which makes them suitable also for controlling nematodes, especially phytopathogenic nematodes.

By virtue of their pronounced microbicidal activity the derivatives of formula I are preferred, wherein the rest R contains a maximum of 25 carbon atoms, among them the derivatives falling under the formula Ia

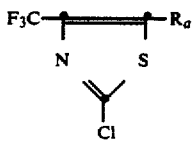

wherein $R_a$ is a radical selected from among cyano, —$COXR_1$, —$CONR_3R_4$ or —COD, X is oxygen or sulfur, $R_1$ is hydrogen; $C_1$-$C_{18}$ alkyl, which is unsubstituted or substituted by halogen, a group cyano, nitro, —$YR_2$, A, —$N(R_3)COA$, —$[NR_{(3)}]_{\overline{m}}CON[(CO)_{\overline{m}}R_3]$—$N(R_3)]_{\overline{m}}(CO)_mR_4$ in which group one of the indices m must be zero, —$C(X)_{\overline{m}}XR_7$, —$(X)_{\overline{m}}CXA$, —$PO(R_5)R_6$, $C_3$-$C_8$cycloalkyl or $C_5$-$C_8$cycloalkenyl, which is unsubstituted or substituted by halogen, $C_1$-$C_4$alkyl or methylenedioxy; $R_1$ further represents $C_3$-$C_8$alkenyl, $C_3$-$C_{18}$cycloalkyl or $C_3$-$C_{18}$cycloalkenyl, which is unsubstituted or substituted by halogen, $C_1$-$C_4$alkoxy, $C_1$-$C_4$alkylthio, $C_1$-$C_4$haloalkoxy, $C_1$-$C_4$haloalkyl, methylenedioxy or —$CO(O)_{\overline{m}}R_7$, —COA, or —$PO(R_5)R_6$; $R_1$ further represents $C_3$-$C_8$alkenyl which is unsubstituted or substituted by halogen or represents —$(E)_mU$ or —$(E)_mQ$, $R_2$ is $C_1$-$C_8$alkyl or $C_3$-$C_8$cycloalkyl, which is unsubstituted or substituted by $C_1$-$C_8$alkoxy, $C_1$-$C_8$alkylthio, $C_2$-$C_8$alkoxyalkyl halogen, cyano or —$CX(X)_mR_7$, —$(X)_m$—$CXA$, —$(X)_mCXR_7$, —$N(R_3)COA$, A, —X-U or XQ; $R_2$ further represents $C_3$-$C_8$alkenyl or $C_3$-$C_8$cycloalkenyl, which is unsubstituted or substituted by halogen or represents —$(E)_{\overline{m}}U$ or —$(E)_{\overline{m}}Q$;

m is zero or one;

Y is oxygen, sulfur, SO or $SO_2$;

A is a radical —$N(R_3)R_4$;

D is a radical —$N(R_3)N(R_4)(CO)_mR_3$;

$R_3$ and $R_4$ independently of each other represent hydrogen, $C_1$-$C_8$alkyl or $C_3$-$C_8$cycloalkyl, which is unsubstituted or substituted by $C_1$-$C_8$alkoxy, $C_2$-$C_8$alkoxyalkoxy, $C_1$-$C_8$alkylthio, cyano, —$COOR_{10}$, $C_1$-$C_4$alkylcarbamoyl, di-$C_1$-$C_4$alkylcarbamoyl, piperidinocarbonyl, pyrrolidinocarbonyl, piperidino or pyrrolidino; $R_3$ and $R_4$ further represent $C_3$-$C_8$alkenyl or $C_3$-$C_8$cycloalkenyl which is unsubstituted or substituted by halogen, $C_1$-$C_8$alkoxy, $C_3$-$C_8$cycloalkyl or cyano, —$COOR_7$, $C_1$-$C_4$alkylcarbamoyl or piperidinocarbamoyl; $R_3$ and $R_4$ represent further $C_3$-$C_8$alkenyl, which is unsubstituted or substituted by U, or $R_3$ and $R_4$ represent a radical —$(E)_{\overline{m}}U$ or —$(E)_{\overline{m}}Q$;

$R_3$ and $R_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine, which may be substituted by halogen, cyano, $C_1$-$C_8$alkoxy, amino, $C_1$-$C_4$alkylamino di-$C_1$-$C_4$alkylamino or —$COOR_7$;

$R_5$ and $R_6$ are independently of each other are hydrogen or $C_1$-$C_4$alkoxy; $R_7$ is hydrogen, $C_1$-$C_8$alkyl, $C_3$-$C_8$cycloalkyl, $C_3$-$C_8$alkenyl, $C_2$-$C_8$alkoxyalkyl, $C_3$-$C_8$alkoxyalkoxyalkyl, $C_1$-$C_4$haloalkyl, —$(C_1$-$C_3$alkylene$)_mU$, —$(C_1$-$C_3$alkylene$)_mQ$, $C_1$-$C_4$haloalkoxy;

U is phenyl or naphthyl, which is unsubstituted or substituted one to three times by halogen, $C_1$-$C_4$alkyl, —Y-$C_1$-$C_4$halkyl, $C_1$-$C_4$haloalkyl, $C_1$-$C_4$haloalkoxy, cyano, nitro, carboxyl, —$COOR_7$, —$CONH_2$, —$CONHR_7$, —$CON(R_7)$, —$SO_2NHR_7$, —$SO_2N(R_7)_2$, pyrrolidino, piperidino, pyrrolidino, carbonyl or piperidinocarbonyl;

E is a $C_1$-$C_8$alkylene or $C_2$-$C_8$alkenylene chain, which is unsubstituted or substituted by halogen, $C_1$-$C_4$alkoxy, $C_1$-$C_4$alkylthio, $C_1$-$C_4$haloalkoxy or by a rest —$CO(O)_mR_7$, —$(CO)_mA$, —$(CO)_mQ$ Q is a heterocycle which is bound via a carbon atom and is selected from among furan, tetrahydrofuran pyran, pentahydropyran, dioxolan, dioxan, benzdioxan, dihydrobenzdioxsan, thienyl, thiazol, which may be substituted by halogen or methyl.

Good microbicidal activity show especially the derivatives of the formula Ib

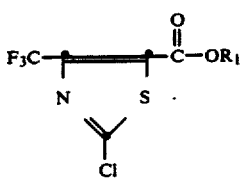

wherein R₁ has the meaning given above.

From U.S. Pat. Nos. 4,199,506, 4,251,261, 4,368,391, 4,437,875 and 4,437,876 are known the 2-chloro-5-trifluoromethyl-thiazol-5-carboxylic acid and derivates wherein $R_1$ is hydrogen, an agriculturally acceptable salt, $C_1$-$C_{10}$alkyl, $C_1$-$C_{10}$haloalkyl, $C_2$-$C_{10}$alkoxyalkyl, $C_2$-$C_{10}$alkenyl, benzyl, Phenyl and chlorophenyl. The other compounds encompassed by formula Ib are new, especially those wherein $R_1$ $C_1$-$C_{18}$ substituted by cyano, nitro, A, —N(R₃)COA, —[N(R₃)]ₘ—CON[(CO)ₘR₃]ₘ—(CO)ₘR₄ wherein at least one of the indices m must be zero, —C(X)ₘXR₇, —(X)ₘCXA, PO(R₃)R₆, $C_1$-$C_8$cycloalkyl or $C_5$-$C_6$cycloalkenyl which is substituted by halogen, $C_1$-$C_4$alkyl or methylenedioxy; $R_1$ is further $C_3$-$C_{18}$cycloalkyl or $C_3$-$C_{18}$cycloalkenyl unsubstituted or $C_3$-$C_8$alkenyl, $C_3$-$C_{18}$cycloalkyl or $C_3$-$C_{18}$cycloalkenyl substituted by halogen, $C_1$-$C_4$alkoxy, $C_1$-$C_4$alkylthio, $C_1$-$C_4$haloalkoxy, $C_1$-$C_4$haloalkyl, methylenedioxy or —CO(O)ₘR₇, —COA, or PO(R₅)R₆; $R_1$ is further $C_3$-$C_8$alkenyl which is unsubstituted or halogen substituted and $R_2$, m, Y, $R_3$, $R_4$, $R_5$, $R_6$ and $R_7$ have the meaning given above.

Also good activity is shown by the derivatives of the formula Ic

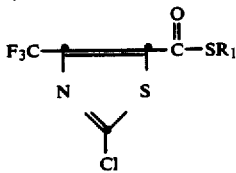

wherein $R_1$ is $C_1$-$C_{18}$alkyl or $C_3$-$C_{18}$cycloalkyl unsubstituted or $C_1$-$C_{18}$alkyl substituted by halogen $C_1$-$C_8$alkoxy, $C_1$-$C_8$alkylthio, $C_2$-$C_8$alkoxyalkoxy nitro, cyano or A—, CX(X)ₘR₇, —N(R₃)COA, A is —N(R₃)R₄ or —(E)ₘU m is zero or one $R_3$ and $R_4$ independently of each other are hydrogen, $C_1$-$C_8$alkyl, $C_3$-$C_8$alkenyl or —(E)ₘ—U or $R_3$ and $R_4$ together with the nitrogen atom to which they are bound form a heterocycle selected from the group consisting of pyrrolidine, piperidine, azepine and morpholine $R_7$ is hydrogen or $C_1$-$C_{10}$alkyl E is a $C_1$-$C_8$alkylene or $C_2$-$C_8$alkenylene chain U is phenyl or naphthyl, which is unsubstituted or substituted by halogen, $C_1$-$C_4$alkoxy or —CO(O)ₘR₇, and X is oxygen or sulfur.

Compounds of the formula Ic, wherein $R_1$ is $C_1$-$C_3$alkyl, phenyl or benzyl are known from U.S. Pat. No. 4,640,702. The other compounds encompassed by formula Ic are new, especially those, wherein $R_1$ is $C_6$-$C_{18}$alkyl or $C_3$-$C_{18}$cycloalkyl unsubstituted or $C_1$-$C_{18}$alkyl or $C_3$-$C_{18}$cycloalkyl substituted by halogen, $C_1$-$C_8$alkoxy, $C_1$-$C_8$alkylthio, $C_2$-$C_8$alkoxyalkoxy, nitro, cyano or A—, CX(X)ₘR₇, —N(R₃)COA, A is —N(R₃)R₄ m is zero or one $R_3$ and $R_4$ independently of each other one hydrogen, $C_1$-$C_8$alkyl, $C_3$-$C_8$alkenyl or —(E)ₘU, $R_3$ and $R_4$ together with the nitrogen atom, to which they are bound form a heterocycle selected from the group consisting of pyrrolidine, piperidine, azepine and morpholine $R_7$ is hydrogen or $C_1$-$C_{10}$alkyl E is a $C_1$-$C_8$alkylene or $C_2$-$C_8$alkenylene chain U is phenyl or naphthyl, which is unsubstituted or substituted by halogen, $C_1$-$C_4$alkoxy or —CO(O)ₘR₇ and X is oxygen or sulfur.

Good microbicidal activity is found with compounds of formula Id

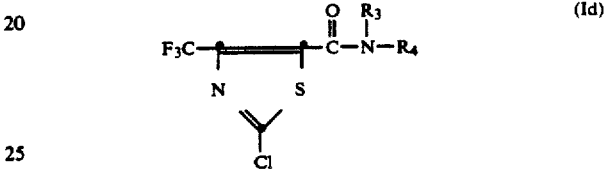

wherein $R_3$ and $R_4$ independently of each other represent hydrogen, $C_1$-$C_8$alkyl or $C_3C_8$cycloalkyl, which is unsubstituted or substituted by $C_1$-$C_8$alkoxy, $C_2$-$C_8$alkoxyalkoxy, $C_1$-$C_8$alkylthio, cyano, —COOR₇, $C_1$-$C_4$alkylcarbamoyl, di-$C_1$-$C_4$alkylcarbamoyl, piperidinocarbonyl, pyrrolidinocarbonyl, piperidino or pyrrolidino; $R_3$ and $R_4$ further represent $C_3$-$C_8$alkenyl or $C_3$-$C_8$cycloalkenyl which is unsubstituted or substituted by halogen, $C_1$-$C_8$alkoxy, $C_3$-$C_8$cycloalkyl or a rest cyano, —COOR₁₀, $C_1$-$C_4$alkylcarbamoyl or piperidinocarbamoyl; $R_3$ and $R_4$ represent further $C_3$-$C_8$alkynyl, which is unsubstituted or substituted by U, or $R_3$ and $R_4$ represent a radical —(E)ₘU or —(E)ₘQ;

$R_3$ and $R_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine, which may be substituted by halogen, cyano, $C_1$-$C_8$alkoxy, amino, $C_1$-$C_8$alkylamino di-$C_1$-$C_4$alkylamino, —COOR₇, $R_7$ is hydrogen, $C_1$-$C_8$alkyl, $C_3$-$C_8$cycloalkyl, $C_3$-$C_8$alkenyl, $C_2$-$C_8$alkoxyalkyl, $C_3$-$C_8$alkoxyalkoxyalkyl, $C_1$-$C_4$haloalkyl, —(C₁—C₃alkylene)ₘU, —(C₁-$C_3$alkylene)ₘQ, $C_1$-$C_4$haloalkoxy;

U is phenyl or naphthyl, which is unsubstituted or substituted one to three times by halogen, $C_1$-$C_4$alkyl, -Y-$C_1$-$C_4$alkyl, $C_1$-$C_4$haloalkyl, $C_1$-$C_4$haloalkoxy, cyano, nitro, —COOR₇, —CONH₂, —CONHR₇, —CONR₇, —SO₂NHR₇, —SO₂N(R₇)₂, pyrrolidino, piperidino, pyrrolidino carbonyl or piperidinocarbonyl;

E is a $C_1$-$C_8$alkylene or $C_2$-$C_8$alkenylene chain, which is unsubstituted or substituted by halogen, $C_1$-$C_4$alkoxy, $C_1$-$C_4$alkylthio, $C_1$-$C_4$haloalkoxy or by a rest —CO(O)ₘR₁₀, —(CO)ₘA, —(CO)ₘQ Q is a heterocycle which is bound via a carbon atom and is selected from among furan, tetrahydrofuran pyran, pentahydropyran, dioxolan, dioxan, benzdioxan, dihydrobenzdioxan, thienyl, thiazol, which may be substituted by halogen or methyl and Y is oxygen sulfur —SO or SO$_2$, especially the compounds 3-chloro-5-[N-(1-cyano-1-methylethyl)-N-methylamido]-4-trifluoromethylthiazol, 3-chloro-5-[N-(1-cyano-cyclohex-1-yl)-N-methylamido]-4-trifluoromethylthiazol, 3-chloro-5-[N-(1-cyano-cyclopent-1-yl)-N-methylamido]-4-trifluoromethylthiazol, 3-chloro-5-(furyl-2-amido)-4-trifluoromethyl-thiazol, 3-chloro-5-(phenyl-eth-1-ylamido)-4-trifluoromethyl-thiazol N,N-Diethyl-2-chloro-4-trifluoromethyl-thiazol-5-carboxamide is known from U.S. Pat. Nos. 4,199,506, 4,437,875, 4,437,876. The other compounds encompassed by formula Id are new. U.S. Pat. No. 3,725,427 discloses 2,4-dimethyl-thiazol-5-carboxamides with fungicidal activity. The compounds of formula Id show improved fungicidal activity over a wider application range.

Excellent microbicidal activity is further shown by the compounds corresponding to the formula Ie

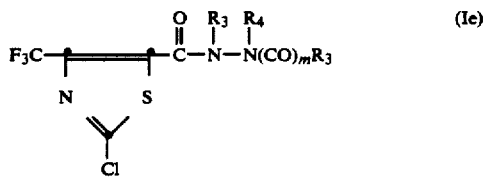

(Ie)

wherein m is 0 or 1 and

R$_3$ and R$_4$ independently of each other are hydrogen, C$_1$–C$_8$alkyl or C$_3$–C$_8$cycloalkyl which is unsubstituted or substituted by C$_1$–C$_8$alkoxy, C$_2$–C$_8$alkoxyalkoxy, C$_1$–C$_8$alkylthio, cyano or —COOR$_7$, C$_1$–C$_4$alkylcarbamoyl or di-C$_1$–C$_4$alkylcarbamoyl or -(E)$_m$U; R$_3$ and R$_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine R$_7$ is hydrogen or C$_1$–C$_8$alkyl E is C$_1$–C$_8$alkylene or C$_2$–C$_8$alkenylene and U is phenyl or naphthyl, which is unsubstituted or substituted one to three times by halogen, C$_1$–C$_4$alkyl, -Y-C$_1$–C$_4$ alkyl, C$_1$–C$_4$haloalkyl, C$_1$–C$_4$haloalkoxy, cyano, nitro, —COOR$_7$, —CONH(R$_7$), SO$_2$NHR$_7$ or SO$_2$N(R$_7$)$_2$ and Y is oxygen, sulfur, SO or SO$_2$, especially 5-(benzoyl-hydrazinocarbonyl)-3-chloro-4-trifluoromethyl-thiazol and 3-chloro-5-(2,4,6-trichlorobenzoylhydrazinocarbonyl)-4-trifluoromethylthiazol.

In these definitions, the alkyl radicals, where not otherwise specified, are understood to have 1 to 18 carbon atoms. They can be straight-chain or branched. The most common radicals are e.g. methyl, ethyl, n-propyl, isopropyl, n-butyl, isobutyl, sec.butyl, tert.butyl, n-pentyl, isopentyl, n-hexyl and n-octyl. The alkenyl and alkenyl radicals can also be straight-chain or branched and contain 3 to 18 carbon atoms. The most commonly used radicals are e.g. allyl, methallyl, butene, butadiene, propynyl, methylproponyl, 1-butynyl and 2-butynyl. Cycloalkyl or cycloalkenyl radicals have preferably 3 to 13 carbon atoms and can also be benzannellated. Typical representatives are e.g. cyclopropyl, cyclopentyl, cyclohexyl, cyclohexenyl, indan, tetrahydronaphthalin, decalin. Halogen stands for fluorine, chlorine, bromine and iodine atoms, especially fluorine and chlorine. Haloalkyl and haloalkenyl radicals are mono- or polysubstituted with halogen atoms.

The above-mentioned radicals may be unsubstituted or substituted, typical substituents of these radicals are e.g. halogen or alkyl, alkenyl, alkenyl, cycloalkyl, aryl or aralkyl radicals that are bound by way of oxygen, sulfur or an amino group. The aryl radicals may be substituted in turn. They may also be bound by may of a sulfinyl-, sulfonyl-, carbonyl-, carbonyloxy-, carbamoyl-, sulfamoyl- or an amino-oxy-bridge to the alicyclic hydrocarbon.

The substituent Q, and also the radicals R$_3$ and R$_4$ with the nitrogen atom, to which they are bound may form an unsaturated or saturated heterocycle with 5 to 12 ring members, which may include one two or three additional heteroatoms or a sulfinyl- or sulfonyl group. They can further contain one or two carbonyl groups and be benzoannellated unsubstituted or substituted.

Suitable heteroatoms are in this context one, two or three additional nitrogen atoms, up to two oxygen or sulfur atoms, which cannot be in vicinal position.

Examples for such heterocycles are listed below: pyrroline, pyrrolidine, imidazoline, imidazolidine, pyrazoline, pyrazolidine, isazoline, isazolidine, oxazoline, oxazolidine, isothiazolidine, thiazoline, thiazolidine, diathiazolidine, oxadiazolidine, piperidine, piperazine, tetrahydropyrimidine and pyrazine, morpholine, thiomorpholine, thiazine, hexahydrotriazine, tetrahydropyrazine, oxadiazine, oxatriazine, hexahydroazepine, hexahydrodiazepine, diazepine, hexahydrodiazepine, azacyclooctan, indoline, isoindoline, benzimidazoline, benzindazoline, benzoxazoline, benzthiazoline, benzisooxazoline, benzthiazole, tetrahydrochinoline, tetrahydroisochinoline, tetrahydrochinazoline, tetrahydrochinoxaline, tetrahydrophthalazine, benzomorpholine, benzothiomorpholine, tetrahydrobenzazepine, tetrahydrobenzdiazepine, tetrahydrobenzoxazepine, 1,5-diabicyclo[4.3.0]nonane, dihydrobenzoxazepine, 1,6-diabicyclo[5.3.0]decane, 1,4-diabicyclo[3.3.0]octane, 1,5-diazabicyclo[4.4.0]decane.

The above heterocycles can also be substituents. Further examples of heterocyclic systems which may occur as substituents are e.g. pyrrole, imidazole, pyrazole, isoxazole, thiazole, triazole, oxadiazole, thiadiazole, tetrazole, oxatriazole, thiatriazole, furan, tetrahydrofuran, dioxole, dioxolane, oxathiole, oxathiolane, thiophen, tetrahydrothiophen, dithiolan, dithiazole, pyridine, pyran, thiopyran, pyridazine, pyrimidine, pyrazine, tetrahydropyran, tetrahydrothiopyran, dioxin, dioxan, dithiin, dithian, oxazine, thiazine, oxathiine, oxathiane, triazine, oxadiazine, thiadiazine, oxathiazine, dioxazine, azepine, oxepin, thiepin, diazepine, oxazepine, indole, benzofuran, benzothiophen, indazole, benzimidazole, benzdioxol, benzdithiol, benzisoxazole, benzthiazole, benzoxazole, benzoxathiole, benztriazole, benzoxadiazole, benzofurazane, benzothiadiazole, quinolin, isoquinolin, chromene, chromane, isochromene, isochromane, thiochromene, isothiochromene, thiochromane, isothiochromane, cinnoline, chinazoline, chinoxaline, phtalazine, benzdioxin, benzdithiin, benzoxazine, benzdioxan, benzoxathiane, benzotriazine, benzazepine, benzdilazepine, benzoxazepine, purine, pteridine, phenoxazine, phenothiazine.

The heterocyclic radicals can be substituted as mentioned above.

Some derivatives of the formula I are known from the literature and can be produced by known methods.

The thiazol derivatives of formula I are produced e.g. according to U.S. Pat. No. 4,199,506, by condensing an acrylic acid ester of the formula II with chlorocarbonyl-sulfonylchloride of the formula III, according to the reaction scheme

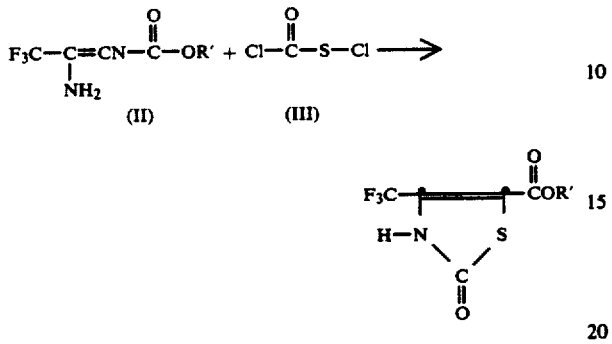

The resulting 2-oxo-4-trifluoromethyl-thiazol-5-carbonic acid derivative is treated with phosphoroxychloride whereby according to the reaction conditions and the amount of phosphoroxychloride used, a 2-chloro-4-trifluoromethyl-thiazol-5-carbonic acid derivative of the formula Ia or 2-chloro-4-trifluoromethyl-thiazol-carbochloride of the formula IIa

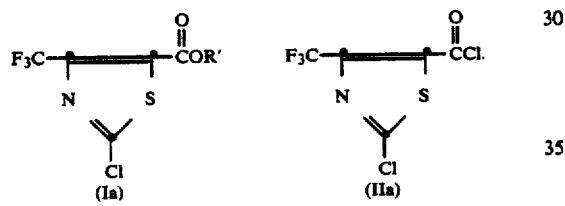

Acrylic acid derivatives of the formula III can be prepared according to J. Het. Chem. 9 (1972) S13 by condensing an acetoacetic ester with trifluoromethylnitril in a boiling solvent in the presence of sodium acetate, according to the reaction scheme

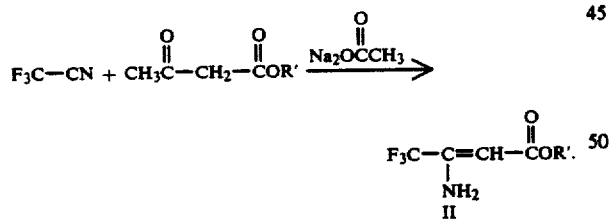

Using 2-chloro-4-trifluoromethyl-thiazol-5-carbochloride of formula IIa, the following active derivatives of formula I can be prepared according to known methods:

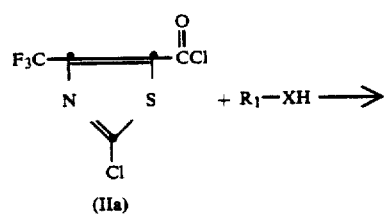

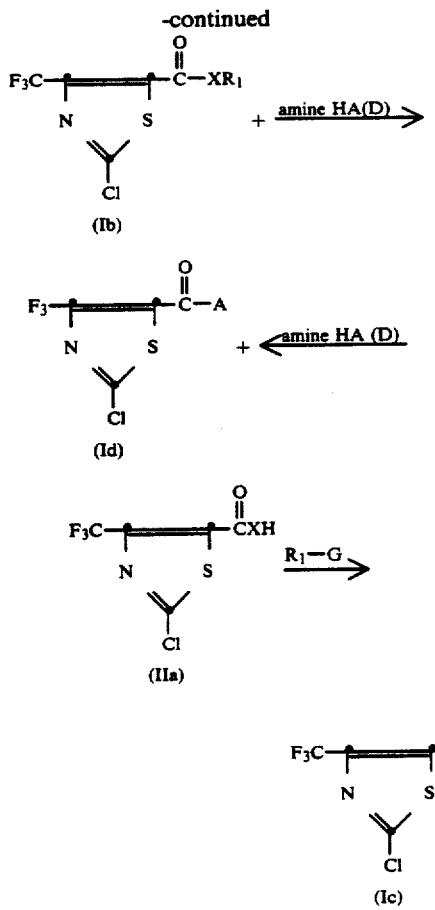

In these formulae A and $R_1$ have the meaning given above under formula Ia and G is an instable nucleofugal rest, such as a halogen atom or a lower-alkyl sulfoxy rest.

In these reactions inert solvents and diluents are used to suit the particular reaction conditions. The following may be mentioned as examples:

halohydrocarbons, especially chlorohydrocarbons, such as tetrachloroethylene, tetrachloroethane, dichloropropane, methylene chloride, dichlorobutane, chloroform, chloronaphthalene, dichloronaphthalene, carbon tetrachloride, trichloroethane, trichloroethylene, pentachloroethane, difluorobenzene, 1,2-dichloroethane, 1,1-dichloroethane, 1,2-cis-dichloroethylene, chlorobenzene, fluorobenzene, bromobenzene, iodobenzene, dichlorobenzene, dibromobenzene, chlorotoluene and trichlorobenzene; ethers, such as ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxan, thioanisole and dichlorodiethyl ether; nitrohydrocarbons, such as nitromethane, nitroethane, nitrobenzene, chloronitrobenzene and o-nitrotoluene; nitriles, such as acetonitrile, butyronitrile, isobutyronitrile, benzonitrile and m-chlorobenzonitrile; aliphatic or cycloaliphatic hydrocarbons, such as heptane, pinane, nonane, cymol, petroleum fractions within a boiling range of from 70° to 190° C., cyclohexane, methylcyclohexane, Decalin, petroleum ether, hexane, ligroin, trimethylpentane, 2,3,3-trimethylpentane and octane; esters, such as ethyl acetate, ethyl acetoacetate and isobutyl acetate; amides, for example formamide, methylformamide and dimethylformamide.

Surprisingly, it has been found that compositions containing the compounds of formula I as active ingredient have, for practical field application purposes, a very advantageous microbicidal spectrum against phytopathogenic fungi and bacteria. Compounds of formula I have very advantageous curative, systemic and, in particular, preventive properties, and can be used for protecting numerous cultivated plants. With the compounds of formula I it is possible to inhibit or destroy the microorganisms which occur in plants or in parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: Fungi imperfecti (e.g. Botrytis, Helminthosporium, Fusarium, Septoria, Cercospora, Pyricularia, Alternaria); Basidiomycetes (e.g. the genera Hemileia, Rhizocotonia, Puccinia); and, in particular, against the class of the Ascomycetes (e.g. Venturia, Podosphaera, Erysiphe, Monilinia, Uncinula). In addition, the compounds of formula I have a systemic action. They can also be used as dressing agents for protecting seeds (fruit, tubers, grains) and plant cuttings against fungus infections as well as against phytopathogenic fungi which occur in the soil.

Apart from their microbicidal activity, the compounds of formula I have nematocidal properties which, in particular, makes them suitable for controlling plant nematodes. For this utility, the compositions of the invention can be used curatively, preventively or systemically. They exhibit a broad range of activity against the various species of nematode and therefore satisfy the requirements of practice.

In the rates of application indicated below, the compounds of the invention, are especially well tolerated by plants.

Accordingly, the invention also relates to microbicidal compositions as well as to the use of the compounds of formula I for controlling phytopathogenic microorganisms, in particular phytopathogenic fungi, or for protecting plants from attack by said microorganisms.

The invention further embraces the preparation of agrochemical compositions, which comprises homogeneously mixing the active ingredient with one or more compounds or groups of compounds described herein. The invention furthermore relates to a method of treating plants, which comprises applying thereto the compounds of formula I or the novel compositions.

Target crops to be protected within the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fiber plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers). This recitation constitutes no limitation.

The compounds of formula I are normally applied in the form of compositions and can be applied to the crop area or plant to be treated, simultaneously or in succession, with further compounds. These compounds can be both fertilizers or micronutrient donors or other preparations that influence plant growth. They can also be selective herbicides, insecticides, fungicides, bactericides, nematicides, mollusicides or mixtures of several of these preparations, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilizers.

A preferred method of applying a compound of formula I, or an agrochemical composition which contains at least one of said compounds, is foliar application. The number of applications and the rate of application depend on the risk of infestation by the corresponding pathogen (species of fungus). However, the compound of formula I can also penetrate the plant through the roots via the soil (systemic action) by impregnating the locus of the plant with a liquid formulation, or by applying the compounds in solid form to the soil, e.g. in granular form (soil application). The compounds of formula I may also be applied to seeds (coating) by impregnating the seeds either with a liquid formulation containing a compound of formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions the methods of application, such as spraying, atomizing, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surfaceactive compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil, sunflower oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverized plant residues. Particularly advantageous application promoting adjuvants which are able to reduce substantially the rate of application are also natural (animal or vegetable) or synthetic phospholipids of the series of the cephalins and lecithins, which can be obtained e.g. from animal or plant cells, in particular from soybeans. Examples of useful physical forms are phosphatidyl choline mixtures. Examples of synthetic phospholipids are dioctanoylphosphatidyl choline and dipalmitoylphosphatidyl choline.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyllaurin salts.

More frequently, however, so-called synthetic surfactants are used, especially fatty sulfonates, fatty sulfates, sulfonated benzimidazole derivatives or alkylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcoholmethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamino-propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilizers, antifoams, viscosity regulators, binders, tackifiers as well as fertilizers or other active ingredients for obtaining special effects.

Such agrochemical compositions constitute an object of the present invention.

The following non-limitative Examples serve to illustrate the invention in more detail. Temperatures are given in Centigrades in the following examples and tables, pressures are given in millibar (mbar), percentages and parts are by weight.

Example 1.1: Preparation of 2-chloro-5-(2-phenoxyethoxycarbonyl)-4-trifluoromethyl-thiazole

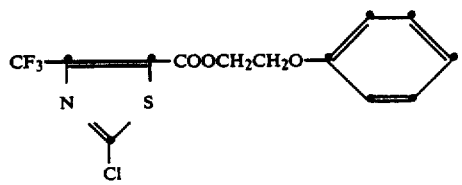

6.3 g (0.045 mol) of 2-phenoxyethanol are added slowly while stirring to a solution of 11 g (0.44 mol) of 2-chloro-5-chlorcarbonyl-4-trifluoromethyl-thiazole in 100 ml of absolute toluene. The solution is then cooled to 0°–5° and 3.6 g (0.045 mol) of triethylamine are added dropwise while stirring. Triethylamine-hydrochloride precipitates from the reaction mixture. After everything is added, the suspension is stirred for 20 hours at room temperature and then poured onto ice-water. The organic phase is separated, dried over sodium sulfate and concentrated in a rotatory evaporator. The residue cristallizes. In order to purify it, the crystals are suspended in petrol-ether, filtered and dried. In this manner 8.7 g (57% of the theoretical yield) of the title compound are obtained, m.p. 70°-72°.

Example 1.2: Preparation of 2-chloro-5-(N-benzyl-N-isopropylamido)-4-trifluoromethyl-thiazole

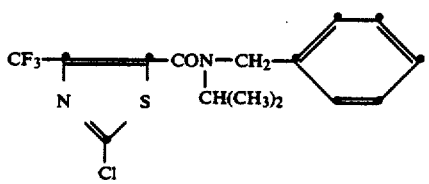

A solution of 2.8 g (0.027 mol) of triethylamine and 4.1 g (0.027 mol) of N-isopropylbenzylamine in 50 ml of ethylacetate are added dropwise at 0° to 5° into a stirred solution of 6.5 g (0.025 mol) of 2-chloro-3-chlorocarbonyl-4-trifluoromethyl-thiazole. After the addition is complete, the reaction mixture, which has turned into a yellow solution is stirred for 15 hours at room temperature and then poured onto ice-water. The organic phase is separated, dried over sodium sulfate, purified with active charcoal, filtered and concentrated on a rotatory evaporator. The residue, a red-brown oil is purified by chromatography in ethyl acetate/hexan over a silica-gel column. After evaporation of the eluant, there remains 6.5 g (73% of the theoretical yield) of a colorless oil with correct chemical analysis.

Example 1.3: Preparation of 2-chloro-5-(1-methoxycarbonyl-eth-1-yloxycarbonyl)-4-trifluoromethyl-thiazole

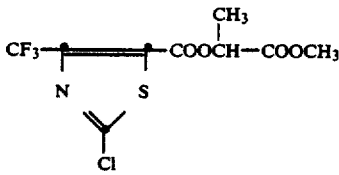

A mixture consisting of 6.94 g of 2-chloro-5-carboxyl-4-trifluoromethyl-thiazole, 5 g of 2-bromopropionic acid-methyl ester and 4.5 g of potassium carbonate, suspended in 50 ml of anhydrous dimethylformamide is stirred under nitrogen atmosphere at room temperature during 3 hours. The reaction-mixture is then filtered and the filtrate is poured into ice-water/ethyl-acetate 1:1. The organic phase is separated, washed 3 times with ice-water, dried and concentrated in a rotatory evaporator. The residue, a colorless oil is distilled for purification. One obtains 8.5 g (75% of the theoretical yield) of title product as colorless oil b.p. 75°-80°/0.015 mbar.

In analogy to these examples the following compounds are prepared:

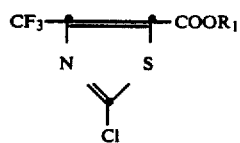

(Ib)

TABLE 1

| No. | $R_1$ | phys. constant |
|---|---|---|
| 1.001 | 1-dodecyl | |
| 1.002 | 1-octadecyl | |
| 1.003 | cyclopropylmethyl | |
| 1.004 | cyclopentylmethyl | |
| 1.005 | cyclohexylmethyl | |
| 1.006 | cyclohexylethyl | |
| 1.007 | tetrahydrofuran-2-yl-methyl | |
| 1.008 | pentahydropyran-2-yl-methyl | m.p. 60–63° |
| 1.009 | 2,2-dimethyl-1,3-dioxolan-4-yl-methyl | oil |
| 1.010 | 1,2-dihydrobenz-1,4-dioxan-2-ylmethyl | resin |
| 1.011 | furan-2-ylmethyl | |
| 1.012 | thiophen-2-ylmethyl | oil |
| 1.013 | 3,4-methylendioxybenzyl | m.p. 96–98° |
| 1.014 | thiophen-2-ethyl | |
| 1.015 | 5-methyl-thiazol-4-ylathyl | m.p. 64–67° |
| 1.016 | phenylethyl | |
| 1.017 | para tolyl-eth-1-yl | oil |
| 1.018 | 3,45-trimethoxybenzyl | |
| 1.019 | geranyl | |
| 1.020 | 2-hexen-1-yl | |
| 1.021 | 1-hexen-6-yl | |
| 1.022 | 1-hexen-3-yl | |
| 1.023 | 2-chloro-2-propen-1-yl | |
| 1.024 | 3-chloro-2-propen-1-yl | |
| 1.025 | 3-phenyl-2-propen-1-yl | |
| 1.026 | cyclopentyl | |
| 1.027 | cyclohexyl | |
| 1.028 | 2-methyl-cyclohexyl | |
| 1.029 | 3-methyl-cyclohexyl | |
| 1.030 | 4-methyl-cyclohexyl | |
| 1.031 | cyclododecyl | |
| 1.032 | 2,3-dimethyl-cyclohexyl | |
| 1.033 | 2,4-dimethyl-cyclohexyl | |
| 1.034 | 2,6-dimethyl-cyclohexyl | |
| 1.035 | 3,5-dimethyl-cyclohexyl | |
| 1.036 | 4-tert.butyl-cyclohexyl | |
| 1.037 | bornyl | m.p. 65–67° |
| 1.038 | norbornyl | oil |
| 1.039 | fenchyl | oil |
| 1.040 | menthyl | oil |
| 1.041 | 2,2-dichlor-cyclopropylmethyl | |
| 1.042 | —CH$_2$—CN | |
| 1.043 | —CH$_2$—CH$_2$—CN | oil |
| 1.044 | —CH$_2$—PO(OC$_2$H$_5$)$_2$ | |
| 1.045 | 2-nitro-ethyl | |
| 1.046 | 2-allyloxy-ethyl | |
| 1.047 | 2-benzyloxy-ethyl | |
| 1.048 | para-chlorbenzyloxyethyl | |
| 1.049 | ortho-chlorbenzyloxyethyl | |
| 1.050 | cyclopropyloxyethyl | |
| 1.051 | cyclohexyloxyethyl | |
| 1.052 | 2-phenoxyethyl | m.p. 70–72° |
| 1.053 | para-chlorphenoxyethyl | |
| 1.054 | —CH$_2$—CH$_2$—SCH$_3$ | |
| 1.055 | —CH$_2$—CH$_2$—SO—CH$_3$ | |
| 1.056 | —CH$_2$—CH$_2$—SO$_2$—CH$_3$ | m.p. 86–88° |
| 1.057 | —CH$_2$—CH$_2$—CH$_2$—SCH$_3$ | |
| 1.058 | —CH$_2$—CH$_2$—CH$_2$—SO—CH$_3$ | |
| 1.059 | —CH$_2$—CH$_2$—CH$_2$—SO$_2$—CH$_3$ | |
| 1.060 | —CH$_2$—CH$_2$—S—C$_4$H$_9$(n) | |
| 1.061 | —CH$_2$—CH$_2$—S—CH$_2$—CH=CH$_2$ | |
| 1.062 | cyclohexylthioethyl | |
| 1.063 | benzylthioethyl | |
| 1.064 | para-chlorbenzylthioethyl | |
| 1.065 | phenylthioethyl | m.p. 47–49° |
| 1.066 | phenylsulfonylethyl | |
| 1.067 | para-tolylthioethyl | |
| 1.068 | para-chlorphenylthioethyl | |
| 1.069 | phenylthiopropyl | |
| 1.070 | β-naphthylthioethyl | |
| 1.071 | 2-phenylthio-1-methyl-ethyl | |

TABLE 1-continued

| No. | $R_1$ | phys. constant |
|---|---|---|
| 1.072 | 2-phenylthio-1-chloromethyl-ethyl | |
| 1.073 | $-CH_2-CH_2-S-CH_2-COOC_2H_5$ | |
| 1.074 | $-CH_2CH_2SCH(CH_3)COOC_2H_5$ | |
| 1.075 | $-CH_2-CH_2-S-CO-N(CH_3)_2$ | |
| 1.076 | piperidinoylthioethyl | |
| 1.077 | $-CH_2-CH_2-S-CS-N(CH_3)_2$ | |
| 1.078 | piperidinothiocarbonylthioethyl | |
| 1.079 | $-CH_2-COOCH_3$ | |
| 1.080 | $-CH_2-COOC_2H_5$ | b.p. 80–85°/ 0.025 mbar |
| 1.081 | $-CH_2-COOC_2H_9(n)$ | |
| 1.082 | $-CH(CH_3)COOCH_3$ | b.p. 25–80°/ 0.015 mbar |
| 1.083 | $-C(CH_3)_2COOC_2H_5$ | |
| 1.084 | $-CH_2-CH_2-COOC_2H_5$ | |
| 1.085 | 5,5-dimethyl-tetrahydrofuran-2-on-3-yl | m.p. 100–102° |
| 1.086 | $-CH_2-CO-N(C_2H_5)_2$ | |
| 1.087 | $-CH_2CON[CH(CH_3)_2]_2$ | |
| 1.088 | $-CH_2CON[CH_2(CH_3)C_2H_5]_2$ | |
| 1.089 | $-CH_2CON(CH_2CH=CH_2)_2$ | |
| 1.090 | 2-methylpiperidinoylmethyl | |
| 1.091 | azepinoylmethyl | oil |
| 1.092 | anilidomethyl | |
| 1.093 | N-methyl-anilidomethyl | |
| 1.094 | N-(2,6-dimethylphenyl)-N-(methoxy-carbonyl-eth-1-yl)-carbamoylmethyl | m.p. 95–97° |
| 1.095 | 1-(piperidinocarbonyl)-eth-1-yl | m.p. 62–66° |
| 1.096 | $-CH_2-CH_2-NH-CO-CH_3$ | |
| 1.097 | cyclopropancarbamoyl-ethyl | |
| 1.098 | $-CH_2-CH_2-NH-CO-CH_2-Cl$ | |
| 1.099 | $-CH_2-CH_2-NH-CO-CHCl_2$ | |
| 1.100 | benzamoyl-ethyl | |
| 1.101 | thienyl-2-carbamoylethyl | |
| 1.102 | furylcarbamoylethyl | |
| 1.103 | $-CH_2-CH_2-NH-CO-NH-CH_3$ | |
| 1.104 | $C(CH_3)_3$ | |
| 1.105 | phenylureylene-ethyl | |
| 1.106 | $-CH_2CH_2N(CH_3)COCH_3$ | |
| 1.107 | $-CH_2CH_2N(CH_3)COCHCl_2$ | |
| 1.108 | $-CH_2CH_2N(CH_3)CONHCH_3$ | |
| 1.109 | $-CH_2CH_2N(CH_2)SO_2CH_3$ | |
| 1.110 | N-methyl-phenylsulfamoyl-ethyl | |
| 1.111 | $-CH_2CH_2N(C_3H_7-i)COCHCl_2$ | |
| 1.112 | $-CH_2CH_2N(CH_2CH=CH_2)CONHCl_2$ | |
| 1.113 | 2-oxo-pyrrolidino-ethyl | m.p. 58–62° |
| 1.114 | dicyclohexylmethyl | |
| 1.115 | α-phenylbenzyl | oil |
| 1.116 | α-methylbenzyl | |
| 1.117 | α-carboxylbenzyl | |
| 1.118 | α-carboxyl-para-chlorbenzyl | |
| 1.119 | α-methoxycarbonyl-benzyl | m.p. 62–64° |
| 1.120 | α-ethoxycarbonyl-benzyl | |
| 1.121 | α-cyanobenzyl | m.p. 78–81° |
| 1.122 | α-benzoyl-benzyl | m.p. 105–109° |
| 1.123 | α-methoxycarbonyl-α-phenylbenzyl | m.p. 106–110° |
| 1.124 | $-CH_2-CH_2-N(CH_3)_2$ | |
| 1.125 | pyrrolidinoethyl | |
| 1.126 | piperidinoethyl | |
| 1.127 | morpholinoethyl | m.p. 185–187° |
| 1.128 | anilinoethyl | (hydrochloride) |
| 1.129 | para (1-methoxycarbonyl)ethoxyphenyl | |
| 1.130 | para(3-methyl-1,3-oxazolidin-2-yl)phenyl | |
| 1.131 | para(N'N'-(dimethyl-ureylene)-phenyl | |
| 1.132 | meta(N',N'-dimethyl-ureylene)phenyl | |
| 1.133 | β-cyano-β-methoxycarbonyl-styryl-4-yl | |
| 1.134 | β,β-di(methoxycarbonyl)-styryl-4-yl | |
| 1.135 | β,β-dicyano-styryl-4-yl | |
| 1.136 | $C_2H_5$ | m.p. 59–60° |
| 1.137 | H | m.p. 122–125° |
| 1.138 | benzyl | m.p. 56–58° |
| 1.139 | (4,4-dimethyl-tetrahydro-fur-3-yl-2-on) | m.p. 100–102° |
| 1.140 | (4-methyl-thiazol-5-ylethyl) | m.p. 64–67° |
| 1.141 | (2,3,5,6-diepoxy-cyclo-hexan-1-yl) syn. isomer | m.p. 144–175° |
| 1.142 | (2,3,5,6-diepoxy-cyclo-hexan-1-yl) anti isomer | m.p. 144–120° |
| 1.143 | α-(4-chlorphenyl)benzyl | |
| 1.144 | α-(2-chlorphenyl)benzyl | |
| 1.145 | α-(4-chlorphenyl)-4-chlorbenzyl | |
| 1.146 | α-(2-chlorphenyl)-2-chlorbenzyl | |
| 1.147 | α-(2-chlorphenyl)-4-chlorbenzyl | |
| 1.148 | α-(4-fluorphenyl)-benzyl | |
| 1.149 | α-(2-fluorphenyl)-benzyl | |
| 1.150 | α-(4-fluorphenyl)-4-fluorbenzyl | |
| 1.151 | α-(2-fluorphenyl)-2-fluorbenzyl | |
| 1.152 | α-(2-fluorphenyl)-4-fluorbenzyl | |
| 1.153 | α-(4-tolyl)-benzyl | |
| 1.154 | α-(4-anisyl)-benzyl | |
| 1.155 | α-(4-methoxyphenyl)-benzyl | |
| 1.156 | α-(3-trifluorphenyl)-benzyl | |

TABLE 2

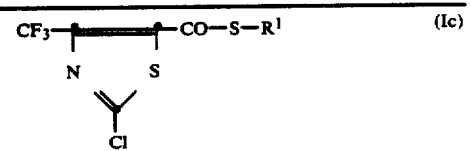
(Ic)

| No. | $R_2$ | phys. constant |
|---|---|---|
| 2.001 | $-CH_2-COOH$ | |
| 2.002 | $-CH_2-COOCH_3$ | |
| 2.003 | $-CH_2-COOC_2H_5$ | |
| 2.004 | $-CH(CH_3)COOH$ | |
| 2.005 | $CH(CH_3)COOC_2H_5$ | |
| 2.006 | $-CH_2-CH_2-COOH$ | |
| 2.007 | $-CH_2-CO-N(C_2H_5)_2$ | |
| 2.008 | piperidinamoylmethyl | |
| 2.009 | azepinamoylmethyl | |
| 2.010 | anilidomethyl | |
| 2.011 | para chloranilidmethyl | |
| 2.012 | 2-carboxyphenylmethyl | |
| 2.013 | benzyl | m.p. 60–62° |

TABLE 3

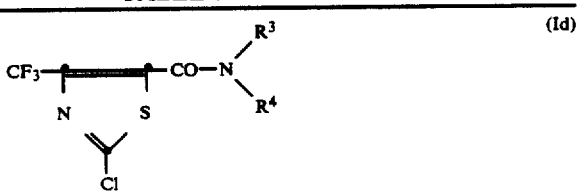
(Id)

| No. | $R_3$ | $R_4$ | phys. constant |
|---|---|---|---|
| 3.001 | allyl | allyl | |
| 3.002 | allyl | 2-methoxy-ethyl | |
| 3.003 | allyl | isopropyl | |
| 3.004 | 2-methyl-2-propen-1-yl | isopropyl | |
| 3.005 | 2-methyl-2-propen-1-yl | cyclohexyl | |
| 3.006 | 2-chlor-2-propen-1-yl | 2-methoxy-ethyl | |

TABLE 3-continued

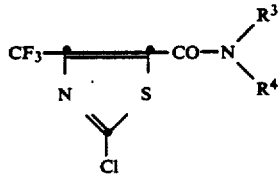

(Id)

| No. | R₃ | R₄ | phys. constant |
|---|---|---|---|
| 3.007 | 2-chlor-2-propen-1-yl | isopropyl | |
| 3.008 | 2-chlor-2-propen-1-yl | cyclohexyl | |
| 3.009 | 2-chlor-2-propen-1-yl | 2-chlor-2-propen-1-yl | |
| 3.010 | 3-chlor-2-propen-1-yl | propyl | |
| 3.011 | propyl | 2-methoxy-ethyl | |
| 3.012 | methyl | cyclohexyl | |
| 3.013 | methyl | benzyl | |
| 3.014 | methyl | 2,6-dichlor-benzyl | m.p. 118–120° |
| 3.015 | isopropyl | benzyl | oil |
| 3.016 | isopropyl | 4-chlor-benzyl | |
| 3.017 | H | benzyl | |
| 3.018 | H | phenyl | |
| 3.019 | methyl | phenyl | |
| 3.020 | methyl | 4-chlor-phenyl | |
| 3.021 | ethyl | 2-chlor-4-brom-phenyl | |
| 3.022 | ethyl | 3-trifluormethyl-phenyl | |
| 3.023 | H | —CH₂—COOC₂H₅ | |
| 3.024 | methyl | —CH₂—COOCH₃ | |
| 3.025 | isopropyl | —CH₂—CO—NH—C₃H₇(i) | |
| 3.026 | cyclopropyl | —CH₂—CO—N(C₂H₅)₂ | |
| 3.027 | ethyl | —CH₂—CH₂—CN | |
| 3.028 | allyl | —CH₂—CH₂—CN | |
| 3.029 | cyclohexyl | —CH₂—CH₂—CN | |
| 3.030 | phenyl | —CH₂—CH₂—CN | |
| 3.031 | phenyl | —CH₂—CH₂—COOH | |
| 3.032 | cyclohexyl | —CH₂—CH₂—COOCH₃ | m.p. 116–120° |
| 3.033 | 2,6-dimethyl-phenyl | —CH(CH₃)COOCH₃ | m.p. 120–123° |
| 3.034 | phenyl | —CH₂—COOH | |
| 3.035 | phenyl | —CH₂—CN | |
| 3.036 | 4-chlor-phenyl | —CH₂—CN | |
| 3.037 | 2,4-dichlor-phenyl | —CH₂—CN | |
| 3.038 | 3,4-dichlor-phenyl | —CH₂—CN | |
| 3.039 | 3-trifluormethyl-phenyl | —CH₂—CN | |
| 3.040 | methyl | 1-cyanocyclopent-1-yl | m.p. 130–133° |
| 3.041 | pyrrolidino | | |
| 3.042 | piperidino | | |
| 3.043 | 2-methylpiperidino | | |
| 3.044 | 2-ethylpiperidino | | |
| 3.045 | hexahydroazepino | | |
| 3.046 | morpholino | | |
| 3.047 | 2,2,5,5-tetramethyl 1,3-oxazolidin-3-yl | | |
| 3.048 | 5,5-dimethyl-2,2-tetra-methylen-1,3-oxazolidin-3-yl | | |
| 3.049 | 5,5-dimethyl-2,2-pentamethylen-1,3-oxazolidin-3-yl | | |
| 3.050 | 2-phenyl-1,3-oxazolidin-3-yl | | |
| 3.051 | 2,2-tetramethylen-benzthiazol-3-yl | | |
| 3.052 | 2-oxo-pyrrolidino | | |
| 3.053 | hexahydro-2-oxo-azepino | | |
| 3.054 | 3-oxo-thiomorpholino | | |
| 3.055 | 2-oxo-1,3-oxazolin-3-yl | | |
| 3.056 | 2-trichloromethyl-1,3-oxazolidin-3-yl | | |
| 3.057 | H | 2-chlorbenzyl | |
| 3.058 | H | 2-hexylbenzyl | |
| 3.059 | C₂H₅ | C₂H₅ | m.p. 40–41° |
| 3.060 | allyl | H | m.p. 56–58° |
| 3.061 | phenylethyl | H | m.p. 88–89° |
| 3.062 | C₂H₅ | 2,6-dichlorbenzyl | m.p. 89–91° |
| 3.063 | 2-chlorobenzyl | H | m.p. 115–116° |
| 3.064 | allyl | allyl | m.p. 100–101° |
| 3.065 | C₄H₉-n | 2,6-dichlorbenzyl | $n_D^{20}$ 1.5491 |
| 3.066 | H | ethoxycroton-2-yl | m.p. 72–74° |
| 3.067 | CH(CH₃)₂ | 2-chlorallyl | $n_D^{20}$ 1.5027 |
| 3.068 | 4-chlor-2-fluor-6-iso-propoxyphenyl | H | m.p. 123–125° |
| 3.069 | cyano-dimethylmethyl | methoxyethyl | m.p. 130–132° |
| 3.070 | chlorphenyl | H | m.p. 125–128° |
| 3.071 | cyano-dimethyl-methyl | H | m.p. 78–80° |
| 3.072 | 2,2-dimethylindanyl | H | m.p. 174–175° |
| 3.073 | 3,5-bistrifluormethylphenyl | H | m.p. 125–127° |
| 3.074 | diphenylmethyl | H | m.p. 177–179° |
| 3.075 | 2,6-difluorophenyl | H | m.p. 160–161° |
| 3.076 | 5-trifluoromethylthiazol-2-yl | H | m.p. 136–138° |

TABLE 3-continued $$CF_3 \begin{array}{c} \phantom{X} \\ \diagup\diagdown \\ N \quad S \\ \diagdown\diagup \\ \overset{|}{C}\!\!-\!\!Cl \end{array} CO\!-\!N \begin{array}{c} R^3 \\ \diagdown \\ \diagup \\ R^4 \end{array} \qquad (Id)$$

| No. | R₃ | R₄ | phys. constant |
|---|---|---|---|
| 3.077 | 2-carboxyl-4-chlorphenyl | H | m.p. 132–134° |
| 3.078 | 3-trifluormethylcyclohexyl | H | m.p. 106–109° |
| 3.079 | 2,4,6-trichlorphenyl | H | m.p. 184–186° |
| 3.080 | furfuryl | H | m.p. 100–102° |
| 3.081 | 3,4-methylendioxybenzyl | H | m.p. 129–131° |
| 3.082 | 4-amidosulfonylphenyl | H | m.p. 186–189° |
| 3.083 | 1,2-diphenyleth-1-yl | H | m.p. 146–148° |
| 3.084 | α-methylbenzyl | H | m.p. 131–133° |
| 3.085 | benzoylamido | H | m.p. 192–194° |
| 3.086 | 4-fluorbenzyl | H | m.p. 128–130° |
| 3.087 | 2,2-diphenyleth-1-yl | H | m.p. 127–129° |
| 3.088 | 1-cyano-cyclopent-1-yl | methoxycarbonylmethyl | m.p. 145–147° |
| 3.089 | 1-cyano-cyclohex-1-yl | H | m.p. 145–147° |
| 3.090 | 2-methoxycarbonyl-4-chlorphenyl | H | |
| 3.091 | 1-cyanocyclopent-1-yl | CH₃ | |

TABLE 4

$$CF_3 \begin{array}{c} \phantom{X} \\ \diagup\diagdown \\ N \quad S \\ \diagdown\diagup \\ \overset{|}{C}\!\!-\!\!Cl \end{array} CO\!-\!\overset{\overset{R^3}{|}}{N}\!\!-\!\!\overset{\overset{R^4}{|}}{N}(CO)_mR\!-\!R^3 \qquad (Ie)$$

| No. | —N(R³)—NR³(CO)ₘR⁴ | phys. constant |
|---|---|---|
| 4.001 | —NH—NH₂ | |
| 4.002 | —NH—N(CH₃)₂ | |
| 4.003 | —N(CH₃)—NHCH₃ | |
| 4.004 | —NH—NHphenyl | m.p. 137–138° |
| 4.005 | —NH—NHCOphenyl | |
| 4.006 | —NH—NHSO₂phenyl | |
| 4.007 | —NH—NH(2,4,6-trichlorphenyl) | m.p. 184–186° |
| 4.008 | —NH—NH(2-chlorphenyl) | |
| 4.009 | —NH—NH(4-chlorphenyl) | |
| 4.010 | —N(CH₃)—NHCO(4-chlorphenyl) | |

2. Formulation Examples for active ingredients of the formula I (% = per cent by weight)

| 2.1 Wettable powders | (a) | (b) | (c) |
|---|---|---|---|
| active ingredient from the Tables 1–3 | 25% | 50% | 75% |
| sodium lignosulphonate | 5% | 5% | — |
| sodium lauryl sulphate | 3% | — | 5% |
| sodium diisobutylnaphthalene-sulphonate | — | 6% | 10% |
| octylphenolpolyethylene glycol ether (7–8 mol ethylene oxide) | — | 2% | — |
| highly dispersed silicic acid | 5% | 10% | 10% |
| kaolin | 62% | 27% | — |

The active ingredient is mixed well with the adjuvants and ground well in a suitable mill. Wettable powders are obtained that can be diluted with water to give suspensions of any desired concentration.

| 2.2 Emulsifiable concentrate | |
|---|---|
| active ingredient from the Tables 1–3 | 10% |
| octylphenolpolyethylene glycol ether (4–5 mol ethylene oxide) | 3% |
| calcium dodecylbenzenesulphonate | 3% |
| castor oil polyglycol ether (35 mol of ethylene oxide) | 4% |
| cyclohexanone | 30% |
| xylene mixture | 50% |

Emulsions of any desired concentration can be prepared from this concentrate by dilution with water.

| 2.3 Dusts | (a) | (b) |
|---|---|---|
| active ingredient from the Tables 1–3 | 5% | 8% |
| talcum | 95% | — |
| kaolin | — | 92% |

Dusts that are ready for use are obtained by mixing the active ingredient with the carriers and grinding in a suitable mill.

| 2.4 Extruder granulate | |
|---|---|
| active ingredient from the Tables 1–3 | 10% |
| sodium lignosulphonate | 2% |
| carboxymethylcellulose | 1% |
| kaolin | 87% |

The active ingredient is mixed with the adjuvants, ground and moistened with water. This mixture is extruded and then dried in a stream of air.

| 2.5 Coated granulate | |
|---|---|
| active ingredient from the Tables 1–3 | 3% |
| polyethylene glycol (MW 200) | 3% |
| kaolin | 94% |
| (MW = molecular weight) | |

The finely ground active ingredient is uniformly applied in a mixer to the kaolin moistened with polyethylene glycol. A dust-free coated granulate is obtained in this manner.

| 2.6 Suspension concentrate | |
| --- | --- |
| active ingredient from the Tables 1-3 | 40% |
| ethylene glycol | 10% |
| nonylphenolpolyethylene glycol ether (15 mol of ethylene oxide) | 6% |
| sodium lignosulphonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants. In this manner, a suspension concentrate is obtained from which suspensions of any desired concentration can be prepared by dilution with water.

3. Biological Examples:

Example 3.1: Action against Puccinia graminis on wheat (a) Residual protective action Wheat plants are treated 6 days after sowing with a spray mixture (0.06% active ingredient) prepared from a wettable powder formulation of the test compound. After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

(b) Systemic action

Wheat plants are treated 5 days after sowing with a spray mixture (0.02% active ingredient, based on the volume of the soil) prepared from a wettable powder formulation of the test compound. After 48 hours the treated plants are infected with a uredospore suspension of the fungus. The plants are then incubated for 48 hours at 95-100% relative humidity and about 20° C. and then stood in a greenhouse at about 22° C. Evaluation or rust pustule development is made 12 days after infection.

Compounds of the Tables 1-3, especially 3.040 exhibit good activity against Puccinia fungi. The Puccinia attack was inhibited almost completely. Puccinia attack is 100% on untreated and infected control plants.

Example 3.2: Action against Cercospora arachidicola on groundnut plants

Residual protective action

Groundnut plants 10-15 cm in height are sprayed with a spray mixture (0.02% of active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected control plants (number and size of the specks=100%), Cercospora attack on groundnut plants treated with compounds of the tables 1-3 is substantially reduced. Thus compound 1.009 inhibits the occurrence of specks almost completely (0 to 10%).

Example 3.3: Action against Erysiphe graminis on barley (a) Residual protective action Barley plants about 8 cm in height are sprayed with a spray mixture (0.006% active ingredient) prepared from a wettable powder formulation of the test compound. The treated plants are dusted with conidia of the fungus after 3 to 4 hours. The infected barley plants are stood in a greenhouse at about 22° C. The fungus attack is evaluated after 10 days.

Compounds of the Tables 1-3 exhibit good activity against Erysiphe fungi. For example, the compounds 1.009, 1.012, 1.065, 1.115, 1.127, 1.137, 3.077, 3.084 and 3.086 inhibited Erysiphe attack almost completely (attack=0-10%). On the other hand, Erysiphe attack is 100% on untreated and infected control plants.

Example 3.4: Residual protective action against Venturia inaequalis on apple shoots Residual protective action Apple cuttings with 10-20 cm long fresh shoots are sprayed with a spray mixture (0.02% a.i.) prepared from a wettable powder formulation of the test compound. The plants are infected 24 hours later with a conidia suspension of the fungus. The plants are then incubated for 5 days at 90-100% relative humidity and stood in a greenhouse for a further 10 days at 20°-24° C. Scab infestation is evaluated 15 days after infection.

Compounds from the Tables 1-3 exhibit good activity against Venturia. Attack is 100% on untreated and infected shoots.

Example 3.5: Action against Botrytis cinerea on beans

Residual protective action

Bean plants about 10 cm in height are sprayed with a spray mixture (0.02%) prepared from the test compound formulated as wettable powder. After 48 hours, the treated plants are infected with a conidia suspension of the fungus. The infected plants are incubated for 3 days at 95-100% relative humidity and 21° C., and evaluation of the fungus attack is then made. Many compounds of Tables 1-3 very strongly inhibit fungus attack. At a concentration of 0.02% compounds 1.004, 1.012, 1.065, 1.115, 1.127, 1.137, 3.077, 3.084 and 3.086 are fully effective (attack 0 to 5%) Botrytis attack on untreated and infect bean plants is 100%.

Example 3.6: Action against Pyricularia oryzae on rice-plants (a) Residual protective action Two week old rice plants are sprayed with a spraying mixture containing 0.006% of active substance, that was prepared from a wettable powder of the substance to be tested. After 48 hours the plants were infested with a suspension containing conidia of the fungus. The infected plants are kept at 24° and 95-100% relative humidity for 5 days before the fungus infestation is evaluated.

(b) Systemic action

Two week old rice plants in flower pots are sprayed with a spraying mixture containing 0.006% of active substance, that was prepared by diluting a wettable powder of the substance to be tested with the required amount of water. The flower pots are then added with water so that the stems of the rice plants stand in water. After 48 hours the plants are infected with a suspension containing conidia of the fungus. The fungus-infectation is evaluated after an incubation period of 5 days during which the rice plants were kept at about 24° and 95–100% relative humidity.

The compounds of tables 1 to 3 are very effective against Pyricularia orizae. The Pyricularia infection is 100% on infected but not treated control plants. The tested compounds, especially 1.115 and 3.040 inhibited fungus attack on rice plants to 0–5%.

Example 3.7: Action against Tilletia caries on wheat

Winter barley of the type Probus is infected with spores of Tilletia caries, to the rate of 3 g of dry fungus-spore per kg of barley seed. The infected seeds are dried and then macerated in a rolling-mixer with an aqueous solution of the compound to be tested, so that 60 ppm of active substance per weight of seed gets applied. The seeds are then dried. The infected and treated barley is sown in October in a field by means of a sowing machine. Lots of 2 m length containing 3 rows are arranged in triple repetition.

The test is evaluated when the spicules are ripe by evaluating the percentage of spicules infested with Tilletia caries.

The compounds of tables 1 to 3 are very effective against Tilletia caries. While plants from infected but not treated seed showed a 100% Tilletia-infestation, infestation, the tested compounds reduced the infection to 0–5%.

Example 3.8: Action against Helminthosporium gramineum on barley

Winter barley of the type "Cl" which is naturally infected with Helminthosporium gramineum is treated in a rolling-mixer with a solution of the compound to be tested, so that 60 ppm per weight of seed get applied.

The infected and treated barley is sown in October in a field by means of a sowing machine, so that lots of 2 m containing 3 rows of plants are arranged in triple repetition.

The test is evaluated when the spicules develop and the percentage of stalks which are infected with Helminthosporium gramineum are counted.

The compounds of tables 1–3 are very effective against Helminthosporium gramineum. While plants from infected but not treated seed showed a 100% Helminthosporium-infection, the tested compounds reduced the infection to 0 to 5%.

Example 3.9: Action against Phytophtora on tomato plants (a) Residual-protective action Three week old tomato-plants are sprayed with a spray-solution containing 0.006% of active substance, which has been prepared from a wettable powder of the substance to be tested. The treated plants are infected with a suspension of sporangia of the fungus. The plants are then kept at 20° and 90–100% relative humidity. The test is evaluated after a 5 day incubation period by evaluation the degree of Phytophthora-infection.

(b) Residual-curative action

Three week old tomato-plants are infected with a suspension of sporangia of Phytophthora. After an incubation period of 22 hours in a humid chamber at 20° and 90–100% relative humidity, the infected plants are dried and sprayed with a spray-solution containing 0.006% of active substance.

The tested compounds of tables 1–3 showed in these test remarkable activity against Phytophtora.

Example 3.10: Action against Rhizoctonia solani (soil fungus) on rice plants (a) Soil application, local protective action 12 days old rice-plants are watered with a spray-solution, made by dilution of a formulation, containing 0.006% of active substance, in such a manner that none of the plant-parts above ground are contaminated. In order to infect the treated plants, a suspension of mycelium and sclerotia of Rhizoctonia solani is poured onto the soil around the plant. After 6 days incubation period at 27° temperature (day) and 23° (night) at 100% relative humidity in a humid-box in the clima-room, the fungus infection on the sheath, the leaves and the stem is estimated.

(b) Leaf application, local protective action 12 days old rice plants are sprayed with a spray-solution, which has been prepared by diluting a formulation with water. After one day the plants are infected by spraying them with a suspension of mycelium and sclerotia of Rhizoctonia solani. After an incubation period of 6 days at a temperature of 27° (day) and 23° (night) at 100% relative humidity in a humid box in the clima-room, the fungus infection on the sheath, the leaves and the stem is evaluated.

The tested compounds of tables 1, 2 and 3 showed in this test good activity against Rhizoctonia solani. Best protection was achieved with compound 3.040.

Example 3.11: Action against Xanthomonas oryzae on rice (Oryza sativa)

(a) Residual protective action 3 week old rice plants of the type "Calora" or "S6" are sprayed in the green-house with a spray-solution containing 0.02% of active substance. After one day when the coating from the spray has dried, the plants are put into a clima chamber of 24° temperature and 75–85% relative humidity, where the are infected. Infection is carried out by cutting the points of the leaves with a scissors, which had been dipped into a suspension of Xanthomonas oryzae. After 10 days incubation period, the best is evaluated. Infected leaves will curl up and become necrotic. The extent of the pathologic symptoms serves to determine tee extent of the residual activity of the substance tested.

(b) Systemic action 3 week old rice plants of the type "Calora" or "S6" are sprayed in the green-house with a spray-solution containing 0.006% of active substance. Three days later the plants are put into a clima-chamber of 24° temperature and 75–85% relative humidity and infected. Infection is carried out by cutting the points of the leaves with a scissors that has been dipped into a suspension of Xanthomonas oryzae. After 10 days incubation period, the test is evaluated. Infected leaves will curl up and become necrotic. The extent of the pathologic symptoms serves to determine the degree of the systemic activity of the substance to be tested.

The tested compounds of tables 1, 2 and 3 showed good activity against Xanthomonas oryzae. The compounds 1.127 and 1.137 reduced the fungies-infection infection to 0–20% while infected not treated control plants were 100% infected.

We claim:

1. A 2-chloro-4-trifluoromethyl-thiazol-5-carbonic acid derivative of the formula Id

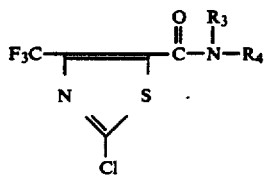 (Id)

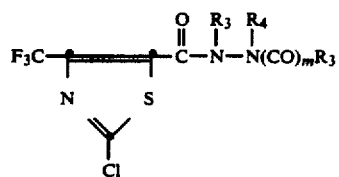 (Ie)

wherein
R$_3$ and R$_4$ independently of each other represent hydrogen or C$_3$-C$_8$cycloalkyl which is unsubstituted of C$_1$-C$_8$alkyl or C$_3$-C$_6$-cycloalkyl which are substituted by C$_1$-C$_8$alkoxy, C$_2$-C$_8$alkoxyalkoxy, C$_1$-C$_8$alkylthio, cyano, —COOR$_7$, C$_1$-C$_4$alkylcarbamoyl, di-C$_1$-C$_4$alkylcarbamoyl, piperidinocarbonyl, pyrrolidinocarbonyl, piperidino or pyrrolidino; R$_3$ and R$_4$ further represent C$_3$-C$_8$alkenyl or C$_3$-C$_8$cycloalkenyl which is unsubstituted or substituted by halogen, C$_1$-C$_8$alkoxy, C$_3$-C$_8$cycloalkyl$_2$cyano, —COOR$_7$, C$_1$-C$_4$alkylcarbamoyl or piperidinocarbamoyl; R$_3$ and R$_4$ represent further C$_3$-C$_8$-alkynyl, which is unsubstituted or substituted by U, or R$_3$ and R$_4$ represent a radical —(E)$_m$—U or —(E)$_m$—Q;

R$_3$ and R$_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine, which may be substituted by halogen, cyano, C$_1$-C$_8$alkoxy, amino, C$_1$-C$_4$alkylamino, di-C$_1$-C$_4$alkylamino, —COOR$_7$, provided that only one of R$_3$ or R$_4$ can be hydrogen, R$_7$ is hydrogen, C$_1$-C$_8$alkyl, C$_3$-C$_8$cycloalkyl, C$_3$-C$_8$alkenyl, C$_2$-C$_8$alkoxyalkyl, C$_3$-C$_8$alkoxyalkoxyalkyl, C$_1$-C$_4$haloalkyl, —(C$_1$-C$_3$alkylene)$_m$U, —(C$_1$-C$_3$alkylene)$_m$Q, C$_1$-C$_4$haloalkoxy;

U is phenyl or naphthyl, which is unsubstituted or substituted one to three times by halogen, C$_1$-C$_4$alkyl, -Y-C$_1$-C$_4$alkyl, C$_1$-C$_4$haloalkyl, C$_1$-C$_4$haloalkoxy, cyano, nitro, —COOR$_7$, —CONH$_2$, —CONHR$_7$, —CONR$_7$, —SO$_2$NHR$_7$, —SO$_2$N(R$_7$)$_2$, pyrrolidino, piperidino, pyrrolidino or piperidinocarbonyl;

E is a C$_1$-C$_8$alkylene or C$_2$C$_8$-alkenylene chain, which is unsubstituted or substituted by halogen, C$_1$-C$_4$alkoxy, C$_1$-C$_4$alkylthio, C$_1$-C$_4$haloalkoxy —CO(O)$_m$R$_7$, —(CO)$_m$A or —(CO)$_m$Q;

Q is a heterocyle which is bound via a carbon atom and is selected from among furan, tetrahydrofuran pyran, pentahydropyran, dioxolan, dioxan, benzdioxan, dihydrobenzdioxan, thienyl, thiazol, which may be substituted by halogen or methyl;

Y is oxygen, sulfur, —SO or SO$_2$

A is —N(R$_3$)(R$_4$) and

M is zero or one.

2. A 2-chloro-4-trifluoromethyl-thiazol-5-carbonic acid derivative according to claim 1 selected from among
3-chloro-5-4-trifluoromethylthiazol,
3-chloro-5-4-trifluoromethylthiazol,
3-chloro-5-4-trifluoromethylthiazol,
3-chloro-5-(furyl-2-amido)-4-trifluoromethyl-thiazol,
3-chloro-5-(phenyl-eth-1-ylamido)-4-trifluoromethyl-thiazol.

3. A 2chloro-4-trifluoromethyl-thiazol-5-carbonic acid derivative of the formula Ie wherein
m is 0 or 1 and
R$_3$ and R$_4$ independently of each other are hydrogen, C$_1$-C$_8$alkyl or C$_3$-C$_8$cycloalkyl which is unsubstituted or substituted by C$_1$-C$_8$alkoxy, C$_2$-C$_8$alkoxyalkoxy, C$_1$-C$_8$alkylthio, cyano or —COOR$_7$, C$_1$-C$_4$ alkylcarbamoyl or di-C$_1$-C$_4$alkylcarbamoyl or —(E)$_m$U; R$_3$ and R$_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine R$_7$ is hydrogen or C$_1$-C$_8$alkyl E is C$_1$-C$_8$alkylene or C$_2$-C$_8$alkenylene and U is phenyl or naphthyl, which is unsubstituted or substituted one to three times by halogen, C$_1$-C$_4$alkyl, -Y-C$_1$-C$_4$alkyl, C$_1$-C$_4$haloalkyl, C$_1$-C$_4$haloalkoxy, cyano, nitro, —COOR$_7$, —CONH(R$_7$), SO$_2$NHR$_7$ or SO$_2$N(R$_7$)$_2$ and Y is oxygen, sulfur, SO or SO$_2$.

4. A 2-chloro-4-trifluoromethyl-thiazol-5-carbonic acid derivative according to claim 3 selected from among 5-(benzoylhydrazinocarbonyl)-3-chloro-4-trifluoromethyl-thiazol and 3-chloro-5-(2,4,6-trichlorobenzoylhydrazinocarbonyl)-4-trifluoromethylthiazol.

5. A method for controlling phytopathogenic microorganisms and for preventing cultivated plants from being attacked by said microorganisms, which comprises applying to the plant, the seed or the locus thereof an effective amount of a 2-chloro-4-trifluoromethyl-thiazol-5-carbonic acid derivative of formula Id

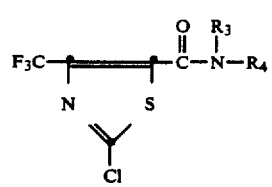 (Id)

wherein
R$_3$ and R$_4$ independently of each other represent hydrogen, C$_1$-C$_8$alkyl or C$_3$-C$_8$cycloalkyl, which is unsubstituted or substituted by C$_1$-C$_8$alkoxy, C$_2$-C$_8$alkoxyalkoxy, C$_1$-C$_8$alkylthio, cyano, —COOR$_7$, C$_1$-C$_4$alkylcarbamoyl, di-C$_1$-C$_4$alkylcarbamoyl, piperidinocarbonyl, pyrrolidinocarbonyl, piperidino or pyrrolidino; R$_3$ and R$_4$ further represent C$_3$-C$_8$alkenyl or C$_3$-C$_8$cycloalkenyl which is unsubstituted or substituted by halogen, C$_1$-C$_8$alkoxy, C$_3$-C$_8$cycloalkyl, cyano, —COOR$_7$, C$_1$-C$_4$alkyl-carbamoyl or piperidinocarbamoyl; R$_3$ and R$_4$ represent further C$_3$-C$_8$alkynyl, which is unsubstituted or substituted by U, or R$_3$ and R$_4$ represent a radical —(E)$_m$—U or —(E)$_m$—Q;

$R_3$ and $R_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine, which may be substituted by halogen, cyano, $C_1$-$C_8$alkoxy, amino, $C_1$-$C_4$alkylamino di-$C_1$-$C_4$alkylamino, —COOR$_7$, $R_7$ is hydrogen, $C_1$-$C_8$alkyl, $C_3$-$C_8$cycloalkyl, $C_3$-$C_8$alkenyl, $C_2$-$C_8$alkoxyalkyl, $C_3$-$C_8$alkoxyalkoxyalkyl, $C_1$-$C_4$haloalkyl, —(C$_1$-C$_3$alkylene)$_m$U, —(C$_1$-C$_3$alkylene)$_m$Q, $C_1$-$C_4$haloalkoxy;

U is phenyl or naphthyl, which is unsubstituted or substituted one to three times by halogen, $C_1$-$C_4$alkyl, -Y-$C_1$-$C_4$alkyl, $C_1$-$C_4$haloalkyl, $C_1$-$C_4$haloalkoxy, cyano, nitro, —COOR$_7$, —CONH$_2$, —CONHR$_7$, —CONR$_7$, —SO$_2$NHR$_7$, —SO$_2$N(R$_7$)$_2$, pyrrolidino, piperidino, pyrrolidino carbonyl or piperidino-carbonyl;

E is a $C_1$-$C_8$alkylene or $C_2$-$C_8$-alkenylene chain which is unsubstituted or substituted by halogen, $C_1$-$C_4$alkoxy, $C_1$-$C_4$alkylthio, $C_1$-$C_4$haloalkoxy, —CO(O)$_m$R$_7$, —(CO)$_m$A, —(CO)$_m$Q Q is a heterocycle which is bound via a carbon atom and is selected from among furan, tetrahydrofuran, pyran, pentanhydropyran, dioxolan, dioxan, benzdioxan, dihydrobenzdioxan, thienyl, thiazol, which may be substituted by halogen or methyl;

Y is oxygen sulfur —SO or SO$_2$;

A is —N(R$_3$)(R$_4$) and m is zero or one.

6. A method according to claim 5 wherein the microorganisms are phytophatogenic fungi or soil borne phytopathogenic bacteries.

7. A method according to claim 5 which comprises treating seeds.

8. A method according to claim 5 which comprises treating rice plants.

9. A composition for controlling phytopathogenic microorganisms and for preventing cultivated plants from attack by said microorganisms, which contains besides inert carrier material compatible with cultivated plants, as active ingredient an effective amount of a 2-chloro-4-trifluoromethylthiazol-5carbonic acid derivative of the formula Id

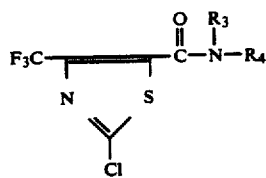

(Id)

wherein $R_3$ and $R_4$ independently of each other represent hydrogen or $C_3$-$C_8$cycloalkyl which is unsubstituted or $C_1$-$C_8$alkyl or $C_3$-$C_6$cycloalkyl which are substituted by $C_1$-$C_8$alkoxy, $C_2$-$C_8$alkoxyalkoxy, $C_1$-$C_8$alkylthio, cyano, —COOR$_7$, $C_1$-$C_4$alkylcarbamoyl, di-$C_1$-$C_4$alkylcarbamoyl, piperidinocarbonyl, pyrrolidinocarbonyl, piperidino or pyrrolidino; $R_3$ and $R_4$ further represent $C_3$-$C_8$alkenyl or $C_3$-$C_8$cycloalkenyl which is unsubstituted or substituted by halogen, lC$_1$-C$_8$alkoxy, $C_3$-$C_8$cycloalkyl, cyano, —COOR$_7$, $C_1$-$C_4$alkylcarbamoyl or piperidinocarbamoyl; $R_3$ and $R_4$ represent further $C_3$-$C_8$-alkynyl, which is unsubstituted or substituted by U or $R_3$ and $R_4$ represent a radical —(E)$_m$U or —(E)$_m$Q;

$R_3$ and $R_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine, which may be substituted by halogen, cyano, $C_1$-$C_8$alkoxy, amino, $C_1$-$C_4$alkylamino, di-$C_1$-$C_4$alkylamino, —COOR$_7$, provided that only one of $R_3$ or $R_4$ can be hydrogen, $R_7$ is hydrogen, $C_1$-$C_8$alkyl, $C_3$-$C_8$cycloalkyl, $C_3$-$C_8$alkenyl, $C_2$-$C_8$alkoxyalkyl, $C_3$-$C_8$alkoxyalkoxyalkyl, $C_1$-$C_4$haloalkyl, —(C$_1$-C$_3$alkylene)$_m$U, —(C$_1$-C$_3$alkylene)$_m$Q, $C_1$-$C_4$haloalkoxy;

U is phenyl or naphthyl, which is unsubstituted or substituted one to three times by halogen, $C_1$-$C_4$alkyl, —Y-$C_1$-$C_4$haloalkyl, $C_1$-$C_4$haloalkoxy, cyano, nitro, —COOR$_7$, —CONH$_2$, —CONHR$_7$, —CONR$_7$, —SO$_2$NHR$_7$, —SO$_2$N(R$_7$)$_2$, pyrrolidino, piperidino, pyrrolidino or piperidinocarbonyl;

E is a $C_1$-$C_8$alkylene or $C_2$-$C_8$-alkenylene chain, which is unsubstituted or substituted by halogen, $C_1$-$C_4$alkoxy, $C_1$-$C_4$alkylthio, $C_1$-$C_4$haloalkoxy, —CO(O)$_m$R$_7$, —(CO)$_m$A, or (—CO)$_m$Q;

Q is a heterocycle which is bound via a carbon atom and is selected from among furan, tetrahydrofuran, pyran, pentahydropyran, dioxolan, dioxan, benzdioxan, dihydrobenzdioxan, thienyl, thiazol, which may be substituted by halogen or methyl;

Y is oxygen, sulfur, —SO or SO$_2$;

A is —N(R$_3$)(R$_4$) and

M is zero or one.

10. A method for controlling phytopathogenic microorganisms and for preventing cultivated plants from being attacked by said microorganisms, which comprises applying to the plant, the seed or the locus thereof, an effective amount of a 2-chloro-4-trifluoromethylthiazol-5-carbonic acid derivative of the formula Ie

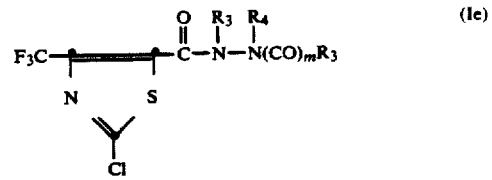

(Ie)

wherein m is 0 or 1 and $R_3$ and $R_4$ independently of each other are hydrogen, $C_1$-$C_8$alkyl or $C_3$-$C_8$cycloalkyl which is unsubstituted or substituted by $C_1$-$C_8$alkoxy, $C_2$-$C_8$alkoxyalkoxy, $C_1$-$C_8$alkylthio, cyano or —COOR$_7$, $C_1$-$C_4$alkylcarbamoyl or di-$C_1$-$C_4$alkylcarbamoyl or —(E)$_m$U; $R_3$ and $R_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine $R_7$ is hydrogen or $C_1$-$C_8$alkyl E is $C_1$-$C_8$alkylene or $C_2$-$C_8$alkenylene and U is phenyl or naphthyl, which is unsubstituted or substituted one to three times by halogen, $C_1$-$C_4$alkyl, —Y-$C_1$-$C_4$alkyl, $C_1$-$C_4$haloalkyl, $C_1$-$C_4$ haloalkoxy, cyano, nitro, —COOR$_7$, —CONH(R$_7$), SO$_2$NHR$_7$ or SO$_2$N(R$_7$)$_2$ and Y is oxygen, sulfur, SO or SO$_2$.

11. A composition for controlling phytopathogenic microorganisms and for preventing cultivated plants from attack by said microorganisms, which contains besides inert carrier material compatible with cultivated plants, as active ingredient, an effective amount of a 2-chloro-4-trifluoromethyl-thiazol-5-carbonic acid derivative of the formula Ie

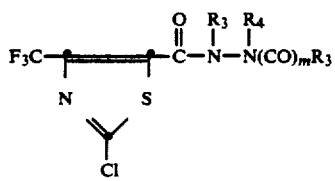

wherein
m is 0 or 1 and
R$_3$ and R$_4$ independently of each other are hydrogen, C$_1$-C$_8$alkyl or C$_3$-C$_8$cycloalkyl which is unsubstituted or substituted by C$_1$-C$_8$alkoxy, C$_2$-C$_8$alkoxyalkoxy, C$_1$-C$_8$alkylthio, cyano or —COOR$_7$, C$_1$-C$_4$alkylcarbamoyl or di-C$_1$-C$_4$alkylcarbamoyl or —(E)$_m$U; R$_3$ and R$_4$ together with the nitrogen atom, to which they are bound form a heterocycle selected from among pyrrolidine, 2-oxo-pyrrolidine, piperidine, morpholine, thiomorpholine, 2-oxo-thiomorpholine and azepine
R$_7$ is hydrogen or C$_1$-C$_8$alkyl
E is C$_1$-C$_8$alkylene or C$_2$-C$_8$alkenylene and
U is phenyl or naphthyl, which is unsubstituted or substituted one to three times by halogen, C$_1$-C$_4$alkyl, —Y-C$_1$-C$_4$alkyl. C$_1$-C$_4$haloalkyl, C$_1$-C$_4$haloalkoxy, cyano, nitro, —COOR$_7$, —CONH(R$_7$), SO$_2$NHR$_7$ or SO$_2$N(R$_7$)$_2$ and
Y is oxygen, sulfur, SO or SO$_2$.

* * * * *